United States Patent [19]

Lundmark

[11] Patent Number: 4,717,375
[45] Date of Patent: Jan. 5, 1988

[54] APPARATUS FOR FOLDING A FLEXIBLE ARTICLE

[75] Inventor: Einar Lundmark, Bålsta, Sweden

[73] Assignee: Mo och Domsjo Aktiebolag, Ornskoldsvik, Sweden

[21] Appl. No.: 935,417

[22] Filed: Nov. 26, 1986

[30] Foreign Application Priority Data

Jan. 8, 1986 [SE] Sweden .............................. 8600074

[51] Int. Cl.$^4$ ............................................... B05B 1/14
[52] U.S. Cl. ................................... 493/360; 493/357; 493/425; 493/427; 493/434; 493/938
[58] Field of Search ............... 493/353, 356, 357, 358, 493/359, 360, 424–428, 431, 434, 435, 442, 444, 454, 938; 270/38, 47, 48, 49, 60, 42–44

[56] References Cited

U.S. PATENT DOCUMENTS

| | | | |
|---|---|---|---|
| 1,536,581 | 5/1925 | Halliwell | 493/360 |
| 2,985,449 | 5/1961 | Dietrich | 493/431 |
| 3,337,211 | 8/1967 | Bilane | 493/357 |
| 3,994,486 | 11/1976 | Ngstrand | 493/427 |
| 4,022,456 | 5/1977 | Hooper et al. | 493/357 |

Primary Examiner—Frederick R. Schmidt
Assistant Examiner—Robert Showalter
Attorney, Agent, or Firm—Sughrue, Mion, Zinn, Macpeak, and Seas

[57] ABSTRACT

The invention relates to apparatus for folding diapers (1) and like articles, in which apparatus the article is advanced to a folding station by a conveyor (2). The folding station includes a driven folding roll (4) which co-acts with a counter roll (9) in a manner to feed the article to at least one driven transport roll (11,12). The transport roll guides the forward end (10) of the article (1) onto the cylindrical surface of a folding roll (16,17) co-acting with the folding roll (4) and intended, in a first folding phase, to be driven in a first transport direction through a given distance up towards the upper part of the folding roll and, during a second folding phase, to be driven in the opposite direction (A) and move the forward part of the article down from the aforementioned upper part. The folding roll is provided with a folding finger arrangement (7) intended for pressing a central part of the article into the nip between the folding roll and the transport roll (12) located therebeneath during the second folding phase.

10 Claims, 7 Drawing Figures

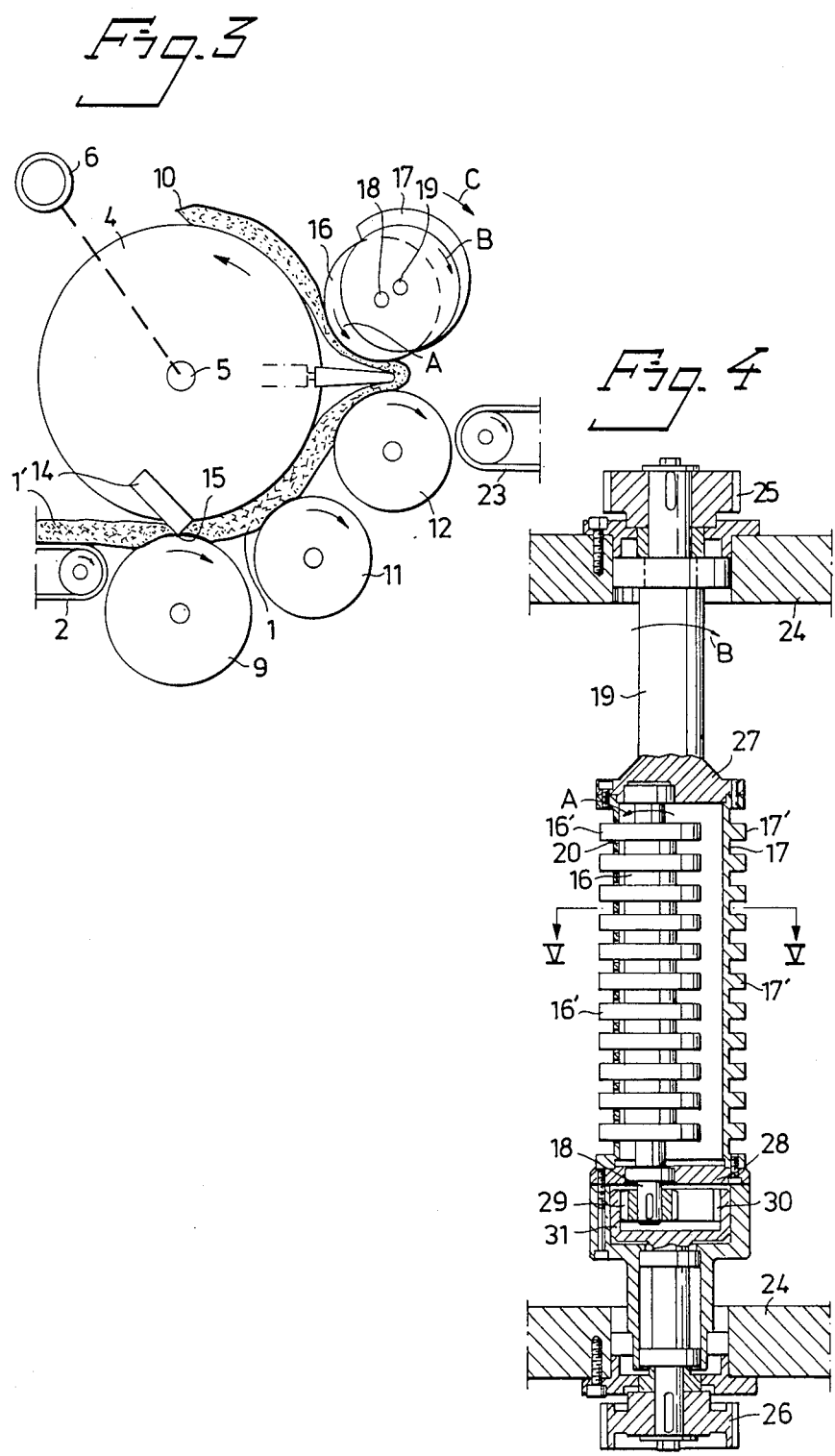

APPARATUS FOR FOLDING A FLEXIBLE ARTICLE

BACKGROUND OF THE INVENTION

The present invention relates to an apparatus for folding a flexible article, such as a diaper, in which the article is advanced in a substantially flat, single-thickness state by conveyor means to a folding station and discharged therefrom in a folded state.

When flat, such flexible articles as diapers, sanitary napkins, liquid absorbent underlays for persons suffering from incontinence, etc., have a size which makes it desirable to fold the articles so that they can be handled more readily. Normally, in this regard, a fold is desired, in which two equally large portions of the article, or substantially equally large parts, are folded one over the other, although it is although possible, for example, to simply fold a small part of the article onto the remaining larger part thereof.

SUMMARY OF THE INVENTION

Accordingly, a main object of the invention is to provide a fast-operating, reliable apparatus which will fold flexible articles of a known kind, the articles either being advanced to the folding station singly or in a continuous string of articles.

According to the apparatus of the invention, a diaper or the like is transported into contact with and around a folding roll with the aid of a portion of a folding roll member rotating in a first direction. After the diaper reaches a certain position on the folding roll, a folding operation is initiated by a finger which is projected from the folding roll and by rotating another portion of the folding roll member in a rotational direction opposite to the other rotational direction to fold the diaper and transport the folded diaper away from the folding roll.

BRIEF DESCRIPTION OF THE DRAWINGS

This object is achieved fully by means of the apparatus described hereinafter with reference to the accompanying drawings, in which FIGS. 1-3 illustrate the various, sequential stages of a folding operation;

FIG. 4 illustrates one embodiment of a folding roll;

DETAILED DESCRIPTION OF THE PREFERRED EMBODIMENTS

Figure 1:
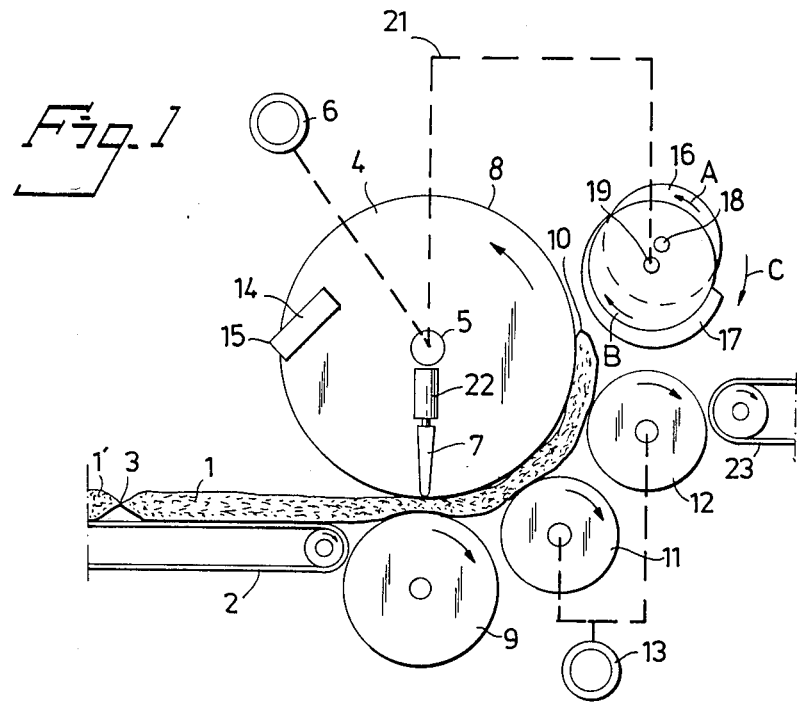
Figure 2:
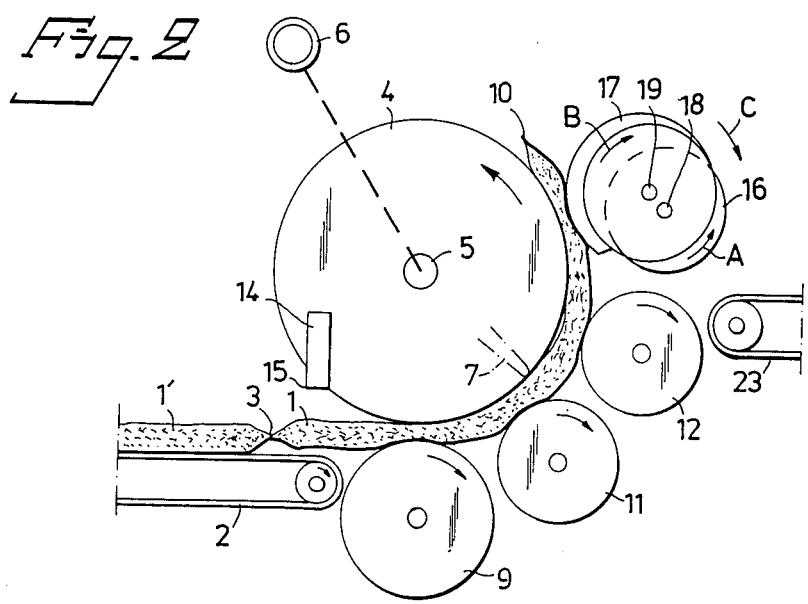

FIGS. 1-3 are highly simplified illustrations of apparatus according to the invention, and illustrate in turn the various steps of folding, for example, a diaper 1, which is advanced to the folding apparatus, for example, on a belt conveyor 2. In the illustrated embodiment the diaper 1 is joined to a following diaper by means of a weld seam 3, separating the diapers 1 from the other. The folding apparatus, which also constitutes a severing device for separating the diaper 1 from the following diaper, by cutting through the weld 3, comprises a cylindrical severing and folding roll 4, which is journalled for rotation on a central shaft 5, which is driven by a motor 6, preferably an electric motor. Journalled for movement in the roll 4 is a folding finger 7, which accompanies the roll 4 during its rotation and which can be projected from the position illustrated in FIG. 1, in which the tip of the finger 7 lies in or beneath the cylindrical surface 8 of the folding roll 4, out to an extended folding position, as described hereinafter. The movement path of the folding finger 7 lies along a radius in the roll 4, and the width of the path, calculated parallel with the shaft or axis 5 of the roll, is preferably equal to the width of the diaper 1, although it may be greater or smaller than said diaper width.

The folding roll 4 co-acts with a counter roll 9, which is preferably driven, and the forward end 10 of the diaper 1 is caught in the nip between the rolls 4 and 9, and transported towards and in contact with the upper part of a first transport roll 11, which feeds and guides the end 10 towards a second transport roll 12 located at a level above the transport roll 11. As with the roll 11, the transport roll 12 is located at a small distance from the cylindrical surface 8 of the folding roll 4. This distance need not be smaller than the thickness of the diaper 1, since the rolls principally have a guiding function and the forward driving force is produced by the rolls 4 and 9. The two transport rolls 11 and 12 are driven, for example, by a motor 13, common to said rolls, and preferably have the same diameters, i.e. mutually the same peripheral speeds. The cylindrical surfaces of the rolls 11, 12, and also the cylindrical surfaces of the remaining rolls, may be coated with a friction enhancing material, for example a thin layer of rubber. Since the principle function of the roll 11 is to guide the diaper, the roll can be replaced with a guide means in the form of a slide bar with low friction characteristics, and can in certain cases be omitted completely. When the folding roll 4 during its anticlockwise rotation in FIG. 1, together with the counter roll 9, which rotates clockwise in FIG. 1, has advanced the end 10 of the diaper to the position illustrated in FIG. 1, the folding finger is located approximately vertically and is directed towards the counter roll 9. When the roll has rotated through about 45°, the roll 4 will have the position illustrated in FIG. 2 and a knife fixedly mounted in the roll 4 and intended to co-act with the counter roll 9 will approach a cutting position, in which the diaper 1 is separated from the following diaper, by cutting through the weld 3 with the edge 15 of the knife 14. To enable the diaper 1 to be folded with the aid of the finger or bar 7, the illustrated embodiment incorporates two folding rolls 16 and 17 which are arranged one within the other, as described in more detail hereinafter. The folding roll 16 is driven in the direction of the arrow A, i.e. anticlockwise in FIG. 1, and the folding roll 17 is driven in the direction of the arrow B, i.e. clockwise in FIG. 1. The roller 16 rotates about a shaft 18 and the roller 17 about a shaft 19. The two folding rolls 16,17 are journalled for co-rotation in the direction of the arrow C about the axis, or shaft, 19 as described hereinafter. The rotational movement of the roll in the direction of arrow C about the shaft 19 is synchronized with the rotation of the folding roll 4, and therewith also rotation of the counter roll 9, with the aid of means not shown, these means possibly comprising, for example, gears which connect the shaft 5 with the shaft 19, illustrated by a transmission line 21 in FIG. 1.

FIG. 2 illustrates the end part of the diaper 1 when captured by the folding roll 17, which during its rotation about the shaft 19 has been moved into contact with the diaper and clamps the diaper firmly against the folding roll 4, and thus draws the diaper upwardly towards the upper part of the roll 4. The folding finger 7 is now located in the position illustrated in FIG. 2. As the roll 17 continues to rotate about the shaft 19, abutment with the diaper progressively decreases and the diaper 1 will finally reach a terminal position, illustrated in FIG. 3. In this position there is activated a hydraulic piston-cylinder device 22 (FIG. 1), which responds by rapidly moving the finger 7 out to the position illustrated in FIG. 3. As the finger 7 is projected from the peripheral surface of the roll 4, the diaper 1 is pressed in between, the folding roll 16, which during rotation around the shaft 19 has reached the illustrated position, and as a result of co-action between the roll 16, which is progressively rotated about the shaft 18, and the transport roll 12 the diaper 1, which in the illustrated embodiment is now folded in two equal parts, is conveyed to a belt conveyor 23, which conveys the folded diaper to a further working station, for example a packaging machine. The finger is retracted immediately after being extended. The knife 14 reaches the clipping position against the counter roll 9 at the same time as the finger 7 is extended, or immediately prior thereto, and severs the diaper 1 from the following diaper, which in FIG. 3 is referenced 1' and which therewith is located in the nip between the rolls 4 and 9 and carried thereby towards the roll 11, whereafter the aforedescribed folding operation is repeated with this diaper.

Figure 5:
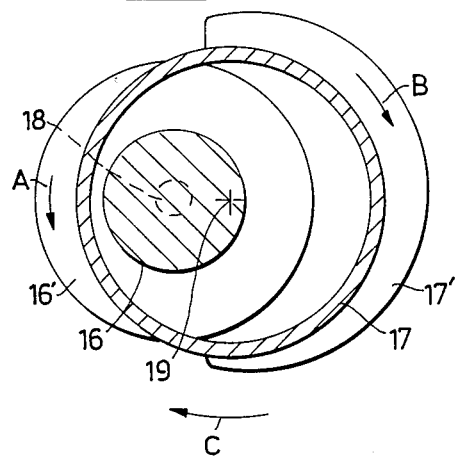
FIG. 5 is an enlarged sectional view taken on the line V—V in FIG. 1.

FIGS. 4 and 5 are detailed views of the folding rolls 16 and 17. The folding roll 17 comprises a cylinder having a plurality of arcuate flanges 17' arranged along the shaft 19, these flanges, in the illustrated embodiment, embracing approximately 180° of the cylindrical surface of the cylinder, as shown in FIG. 5. When seen in the direction of rotation B, each flange, or cam 17', has a leading edge which is lower than the trailing edge, and thus when the diaper 1 is captured for folding, will progressively engage the diaper with greater force so as to drive the diaper upwards in accordance with FIG. 1. The cylindrical surface of the roll 17 is provided with through-passing slots 20 located substantially diametrically opposite the cams 17'. Projecting through each such slot 20 is part of the drive ring 16', said ring being arranged on a cylindrical roll 16, which is journalled for rotation in the folding roll 17 on the shaft 18. The shaft 19 is journalled in the machine frame 24 and carries on one end a gear drive 25, to which a drive force is applied from the transmission line 21 in FIG. 1. The illustrated embodiment also incorporates a gear drive 26, which is also driven from the transmission line 21. As will be seen from FIGS. 4 and 5, the folding roll 16 is journalled eccentrically in the folding roll 17. One end of the shaft of the folding roll 16 is rotatably journalled in an end plate 27 on the folding roll 17, while the other end of the shaft is rotatably journalled in a further end plate 28 on the folding roll 17. This other end of the shaft carries a drive 29 which co-acts with the inner teeth 30 of a gear wheel 31, which is rotatably journalled in the folding roll 17 and which is driven from the aforesaid drive 26. Thus, the folding roll 16 is driven about its own shaft 18 and executes rotational movement about the shaft 19 of the folding roll 17 as the roll 17 rotates. As will be understood, the speed of rotation about the shaft 18 is greater than the speed of rotation about the shaft 19, so that the diaper 1 is drawn downwards and fed-out, in the manner illustrated in FIG. 3, i.e. the peripheral speed in direction A must be greater than the peripheral speed in direction C of the folding roll 17, and preferably coincides with the peripheral speed of the transport roll 12.

Figure 6:
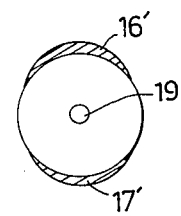
FIG. 6 illustrates a modified folding roll.

Although the aforedescribed folding arrangement incorporating double folding rollers 16,17 is the one preferred, it is also possible to use a single, reversible folding roll which, during a first phase in which the diaper is advanced up on the roll 4 according to FIGS. 1 and 2, is rotated in the direction of the arrow B and during a second phase is rotated in the direction of the arrow A. In order to obtain rapid reversal in the feed direction, such a roll should have but small mass and is preferably made of a light metal. When seen at right angles to the rotational axis, the roll should have an approximately elliptical cross-sectional shape, as shown in FIG. 6, in which the parts lying against the diaper 1 have been illustrated with the driving parts 16' and 17' according to FIG. 5.

Naturally, in this case there is found only one single rotational shaft corresponding to the rotational shaft 18 of FIG. 5.

Figure 7:
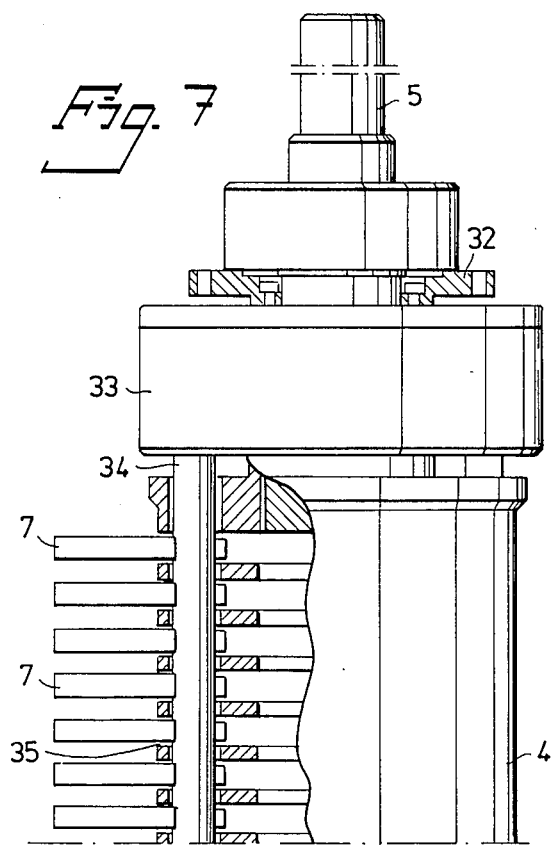
FIG. 7 illustrates part of a folding roll.

FIG. 7 illustrates a folding roll 4, provided with a modified folding finger arrangement. The shaft 5 of the folding roll 4 is driven by the motor 6 illustrated in FIG. 1, via a gear drive 32, and is connected to a planetary gear 33 which rotates together with the folding roll 4. The planetary gear 33 is arranged to drive a shaft 34 rotatably journalled in the interior of the folding roll 4. The shaft 34 is provided with a plurality of folding fingers 7 which, during rotation of the shaft 34, can be swung out through slots 35 located in the roll 4, one such slot being provided for each finger. In FIG. 7 the fingers 7 are shown in a fully outwardly swung position, which corresponds to the position of the finger 7 in FIG. 3. Subsequent to rotation of the shaft 34 through 180° from the position illustrated in FIG. 7, the fingers 7 are located completely within the roll 4. The relative rotation between the roll 4 and the shaft 34 is adapted so as to obtain a folding function in accordance with FIGS. 1–3.

It is emphasized that the constructional elements illustrated schematically in the aforegoing have been shown merely to illustrate the function of the arrangement, and that many modifications can be made within the scope of the claims. For example, the described arrangement of apparatus can be utilized in folding diapers or other flexible articles advanced separately to the folding station, thereby obviating the need for a cutting or severing function, and possibly also the need for the transport roll 11.

The fingers 7 of the FIG. 7 embodiment can also be replaced with a single bar projecting out from the shaft 34, in which case the cylindrical surface of the roll 4 is provided with an aperture corresponding to the length of the bar.

The roll 4 illustrated in FIGS. 1–3, which in addition to the finger arrangement is also provided with a knife 14, has been found particularly suitable, since it enables the production rate to be substantially increased. In addition, as before indicated it is presumed to use a knife 14 having a straight cutting edge 15, the whole length of which is brought into immediate engagement with the counter roll 9 and therewith sever one diaper from another. It is a well known fact that the edge of a cutting knife used in such cutting techniques becomes swaged or likewise deformed in the passage of time, i.e. burrs are formed on both sides of the edge which hook into the article 1 and lift the same. This drawback has been turned to advantage in the illustrated embodiment, since these burrs lift up the forward part of the diaper, as seen in the feed direction, and thus automatically guide said diaper part upwards into contact with the roller 12 and the cylindrical surface of the roll 4.

I claim:

1. Apparatus for folding a flexible article (1). for example a diaper, in which the article is advanced in a transport direction and in a substantially flat state by conveyor means (2) to a folding station and discharged from said station in a folded state, characterized in that the folding station includes a driven main folding roll (4) which co-acts with an underlying counter roll (9), said two rolls defining therebetween a nip for capturing and further transport of the article from the conveyor (2) to at least one driven transport roll (11,12) intended for guiding the forward end (10) of the article (1), as seen in the transport direction, onto a first arcuate surface of a first portion of a folding roll member (16,17) for co-acting with the main folding roll (4), the first portion of the folding roll member being arranged to be driven in a first folding phase in a first rotational direction (B) and for frictionally engaging the first arcuate surface with the article (1) to transport said article through a given distance up against the upper part of the main folding roll (4) and, the folding roll member having a second portion, with a second arcuate surface, for co-acting with the main folding roll during a second folding phase, and for being driven in a second rotational direction (A) opposite to the first rotational direction and for frictionally engaging the second arcuate surface with the article to move the forward part of said article, as seen in the transport direction, down from the upper part of the main folding roll; and arranged in the interior of the main folding roll (4) is a folding-finger device (7) which, during said second folding phase, is intended to be moved by drive means (22; 34) out from the main folding roll so as to press a central part of the article (1) into the nip between the folding roll member (16,17) and the transport roll (12) located therebeneath.

2. Apparatus according to claim 1 in which the articles (1) advanced to the folding arrangement are joined together in a continuous string, characterized in that the main folding roll (4) is provided with a knife (14), the cutting edge (15) of which projects beyond the cylindrical surface (8) of the main folding roll (4) and, during rotation of the main folding roll (4), is arranged to co-act with the counter roll (9) in a manner to sever one article (1) from another.

3. Apparatus according to claim 1 or 2, characterized in that the folding-finger device (7) includes at least one finger intended, during said second folding phase, to be moved by drive means (22) radially outwards from the cylindrical surface of the folding roll (4) in a direction towards said gap between the main folding roll member (16,17) and the transport roll (12) located therebeneath.

4. Apparatus according to claim 1 or 2, characterized in that the folding-finger arrangement includes a driven shaft (34) journalled for rotation in the interior of the main folding roll (4) and having a finger element (7), and at least one aperture (35) which is located in the cylindrical surface (8) of the main folding roll (4) and which permits the finger element (7) to swing out from the said cylindrical surface during rotation of the shaft (34).

5. Apparatus according to claim 4, characterized in that the finger element comprises a plurality of mutually spaced and mutually parallel fingers (7); and in that an aperture (35) is provided in the cylindrical surface (8) of the main folding roll (4) for each finger.

6. Apparatus according to claim 1, characterized in that the first portion of the folding roll member comprises a first roll (17) which is intended to be driven in the first rotational direction (B) for transporting the article through said given distance, and the second portion of the folding roll member comprises a second roll (16) which is rotatably journaled in the first roll (17) and the first roll has an outer peripheral surface, along which said first arcuate surface is provided, for defining at least one opening therein along a longitudinally extending part thereof through which the second roll (16) projects.

7. Apparatus according to claim 6, characterized in that the second roll (16) is provided with rings (16') which are mutually spaced in the axial direction of the roll, an outer periphery of the rings forming said second arcuate surface; and in that the one opening in the peripheral surface of the first roll (17) comprises slots which extend in the peripheral direction of the roll, each of said slots being provided for each ring, respectively.

8. Apparatus for folding a flexible article (1), for example a diaper, in which the article is advanced in a transport direction and in a substantially flat state by conveyor means (2) to a folding station and discharged from said station in a folded state, characterized in that the folding station includes a driven main folding roll (4) which co-acts with an underlying counter roll (9), said two rolls defining therbetween a nip for capturing and further transport of the article from the conveyor (2) to at least one driven transport roll (11,12) intended for guiding the forward end (10) of the article (1), as seen in the transport direction, onto a first arcuate surface of a first portion of a folding roll member (16,17) for co-acting with the main folding roll (4), the first portion of the folding roll member being arranged to be driven in a first folding phase in a first rotational direction (B) and for frictionally engaging the first arcuate surface with the article (1) to transport said article through a given distance up against the upper part of the main folding roll (4) and, the folding roll member having a second portion, with a second arcuate surface, for co-acting with the main folding roll during a second folding phase, and for being driven in a second rotational direction (A) opposite to the first rotational direction and for frictionally engaging the second arcuate surface with the article to move the forward part of said article, as seen in the transport direction, down from the upper part of the main folding roll; and arranged in the interior of the main folding roll (4) is a folding-finger device (7) which, during said second folding phase, is intended to be moved by drive means (22; 34) out from the main folding roll so as to press a central part of the article (1) into the nip between the folding roll member (16,17) and the transport roll (12) located therebeneath, wherein the first and second portion of the folding roll member have a common axis of rotation.

9. Apparatus for folding a flexible article (1), for example a diaper, in which the article is advanced in a transport direction and in a substantially flat state by conveyor means (2) to a folding station and discharged from said station in a folded state, characterized in that the folding station includes a driven main folding roll (4) which co-acts with an underlying counter roll (9), said two rolls defining therebetween a nip for capturing and further transport of the article from the conveyor (2) to at least one driven transport roll (11,12) intended for guiding the forward end (10) of the article (1), as seen in the transport direction, onto a first arcuate surface of a first folding roll for co-acting with the main folding roll (4), the first folding roll being arranged to be driven in a first folding phase in a first rotational direction (B) and for frictionally engaging the first arcuate surface with the article (1) to transport said article through a given distance up against the upper part of the main folding roll (4), a second folding roll, having a second arcuate surface, for co-acting with the main folding roll during a second folding phase, and for being driven in a second rotational direction (A) opposite to the first rotational direction and for frictionally engaging the second arcuate surface with the article to move the forward part of said article, as seen in the transport direction, down from the upper part of the main folding roll; and arranged in the interior of the main folding roll (4) is a folding-finger device (7) which, during said second folding phase, is intended to be moved by drive means out from the main folding roll so as to press a central part of the article (1) into the nip between the second folding roll and the transport roll (12) located therebeneath, wherein the first and second folding rolls are rotatably coupled.

10. Apparatus for folding a flexible article (1), for example a diaper, in which the article is advanced in a transport direction and in a substantially flat state by conveyor means (2) to a folding station and discharged from said station in a folded state, characterized in that the folding station includes a driven main folding roll (4) which co-acts with an underlying counter roll (9), said two rolls defining therebetween a nip for capturing and further transport of the article from the conveyor (2) to at least one driven transport roll (11,12) intended for guiding the forward end (10) of the article (1), as seen in the transport direction, onto a first arcuate surface of a first portion of a folding roll member (16,17) for co-acting with the main folding roll (4), the first portion of the folding roll member being arranged to be driven in a first folding phase in a first rotational direction (B) and for frictionally engaging the article (1) between the first arcuate surface and the main folding roll to transport said article through a given distance up against the upper part of the main folding roll (4) and, the folding roll member having a second portion, with a second arcuate surface, for co-acting with the main folding roll during a second folding phase, and for being driven in a second rotational direction (A) opposite to the first rotational direction and for frictionally engaging the article between the second arcuate surface and the main folding roll to move the forward part of said article, as seen in the transport direction, down from the upper part of the main folding roll; and arranged in the interior of the main folding roll (4) is a folding-finger device (7) which, during said second folding phase, is intended to be moved by drive means (22; 34) out from the main folding roll so as to press a central part of the article (1) into the nip between the folding roll member (16,17) and the transport roll (12) located therebeneath.

* * * * *